(12) United States Patent
Germond

(10) Patent No.: US 7,024,951 B2
(45) Date of Patent: Apr. 11, 2006

(54) METHOD OF SAMPLING FROM A MULTIPHASE FLUID MIXTURE, AND ASSOCIATED SAMPLING APPARATUS

(75) Inventor: Baptiste Germond, Chatenay Malabry (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 135 days.

(21) Appl. No.: 10/471,129

(22) PCT Filed: Apr. 12, 2002

(86) PCT No.: PCT/EP02/04145

§ 371 (c)(1),
(2), (4) Date: Jan. 26, 2004

(87) PCT Pub. No.: WO02/086455

PCT Pub. Date: Oct. 31, 2002

(65) Prior Publication Data

US 2004/0112150 A1 Jun. 17, 2004

(51) Int. Cl.
*G01N 1/16* (2006.01)
(52) U.S. Cl. .................................................. 73/863.21
(58) Field of Classification Search ............ 73/863.21, 73/61.44
See application file for complete search history.

(56) References Cited

U.S. PATENT DOCUMENTS

| 3,824,858 A | 7/1974 | Erdman |
| 5,654,502 A | 8/1997 | Dutton |
| 6,182,505 B1 | 2/2001 | Segeral |
| 2003/0159986 A1 | 8/2003 | Amado et al. |

Primary Examiner—Hezron Williams
Assistant Examiner—Rodney Frank
(74) Attorney, Agent, or Firm—Victor H. Segura; Brigitte L. Echols

(57) ABSTRACT

The invention relates to a method of sampling a fluid phase in a multiphase fluid mixture flowing in a pipe (7) under given pressure conditions (P), said method comprising the following steps; admitting the multiphase fluid mixture into a phase separator (9); separating the multiphase fluid mixture so as to isolate the fluid phase for sampling; pressurizing a sampling device (10) to the given pressure in the pipe (7); and recovering a sample of said fluid phase in said sampling device. According to the invention, the method further comprises a step of increasing the pressure in the phase separator (9) in successive stage until said pressure in the separator reaches the give pressure (P) in the pipe (7). The invention also provides a sampling apparatus for taking a fluid phase from a multiphase fluid mixture flowing in a pipe (7) under given pressure conditions (P), said apparatus comprising: a phase separator (9); admission means (11, 12a) for admitting the multiphase fluid mixture into said separator; and sampling means (10) for taking a sample of said fluid phase, said sampling means being connected to the phase separator. According to the invention, the apparatus further comprises closure means (8a, 8b, 8c) for increasing the pressure inside the separator (9) in successive stages.

14 Claims, 1 Drawing Sheet

Figure 1:
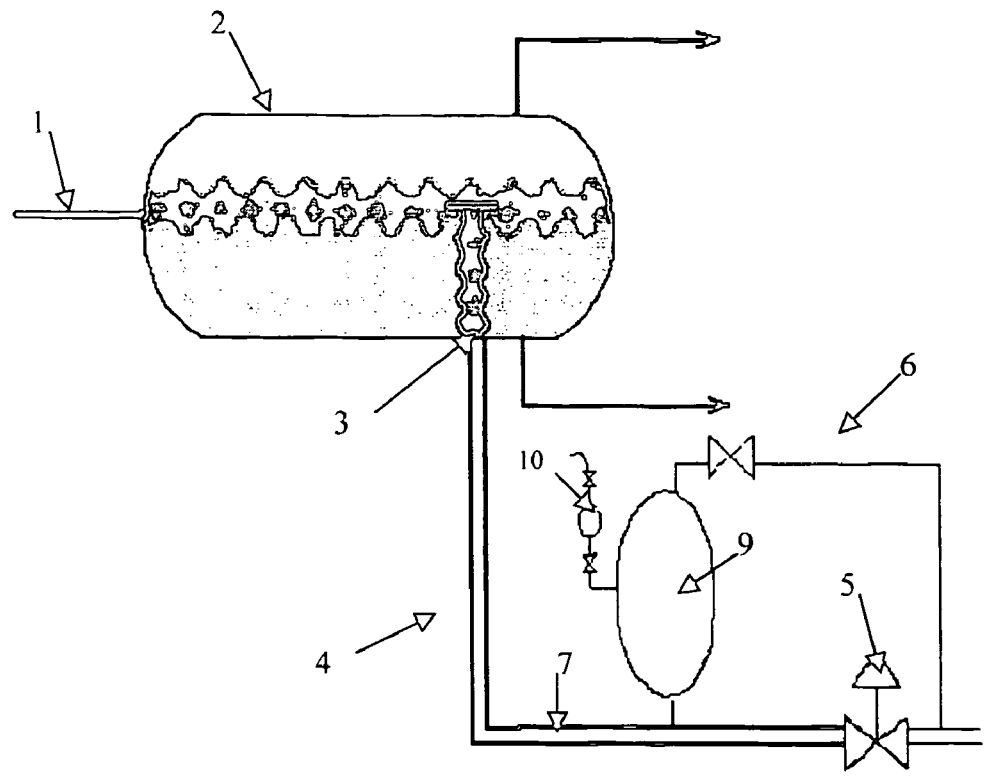

METHOD OF SAMPLING FROM A MULTIPHASE FLUID MIXTURE, AND ASSOCIATED SAMPLING APPARATUS

The present invention relates to a method of sampling a fluid phase from a multiphase fluid mixture, and to associated sampling apparatus. A preferred application of the invention relates to a method of taking a sample in order to measure the density of an oil coming from the effluent of an oil well, and to do so under conditions of temperature and pressure that correspond to those of the line for enabling said effluent to be transported.

After a hydrocarbon well has been drilled and made safe, the well is put into production in order to identify clearly the nature and the magnitude of its components. These tests, commonly referred to as "well testing", are particularly important for future working of the oil deposit since they make it possible to estimate its capacity for hydrocarbon production and thus the yield of the well.

It is common practice for these tests to make use of means for separating the various phases of the effluent (water, oil, and gas). Since the various phases are of different densities, separation is performed continuously in a separator where the phases settle. Downstream from the separator, the aqueous phase is discarded, possibly after additional purification, and the hydrocarbons are burned off, stored, or injected into another pipe. The measurements that are performed serve to determine the flow rate of the various phases under the temperature and pressure conditions of the separator. Thereafter, in order to provide these flow rates under "commercial" well operating conditions, i.e. under conditions of temperature and pressure close to atmospheric conditions, and in units that are meaningful to the well operator (typically volume flow rates corresponding to a daily number of barrels of oil and a daily volume of gas), it is necessary to make corrections to "transform" these flow rates as commonly provided by measuring instruments.

To provide the most accurate possible data concerning oil production volume flow rate from a well, various problems arise. Firstly, it is necessary to manage to take a sample of oil that is pure, i.e. that is not "polluted" by the other phases. This is particularly difficult when using outlet separators in which the water content of the oil phase can be as much as 30%, e.g. the separator that constitutes the subject matter of French patent application No. 00/05666 filed May 3, 2000 in the name of the Applicant. Another problem lies in the difficulty in taking the oil sample under the temperature and pressure conditions of the separator. Since the pressure conditions of the separator are higher than those of the atmosphere, care must be taken to take an oil phase sample without decompressing it since that would lead to an unusable sample containing "dead" oil (i.e. oil deprived of its gas).

An object of the invention is to remedy those drawbacks by proposing a sampling method for collecting a fluid phase from a multiphase fluid mixture without changing the thermodynamic conditions of the mixture.

To this end, the invention provides a method of sampling a fluid phase in a multiphase fluid mixture flowing in a pipe under given pressure conditions, said method comprising the following steps:
   admitting the multiphase fluid mixture into a phase separator;
   separating the multiphase fluid mixture so as to isolate the fluid phase for sampling;
   pressurizing a sampling device to the given pressure in the pipe; and
   recovering a sample of said fluid phase in said sampling device.

According to the invention, the method further comprises a step of increasing the pressure in the phase separator in successive stages until said pressure in the separator reaches the give pressure in the pipe.

In the invention, the step of increasing of pressure by successive stages is performed simultaneously with the step of admitting the multiphase fluid mixture into the separator.

In this way, the method of the invention makes it possible to collect a fluid phase without changing thermodynamic conditions between the pipe and the sampling device. The method is thus particularly suitable when the sample collected in this way is for use in performing accurate measurements concerning the mixture as it is when flowing along the pipe, and not as it is under "artificial" operating conditions. Furthermore, since the separation step takes place in a separator that is not subjected to the flow rate conditions of the pipe, separation times can be considerably lengthened, thereby guaranteeing the purity of the sampled fluid phase. Thus, by maintaining the same pressure conditions all along the method, from the multiphase mixture of fluids to the fluid phase which is to be sampled, it is possible to use said method for recovering a pure oil phase sample from an effluent coming from an oil well, and to do so without falsifying the measurements taken on the sample, which sample does not contain any "dead" oil specifically because of the constant pressure. The method of the invention is thus particularly effective during well testing operations of the kind mentioned above or for any sampling from a pipe that is exporting an effluent.

In an advantageous implementation of the invention, the phase separator comprises a separator in which the phases settle under gravity and the sampling device comprises a sampling flask and admission means, said admission means being connected to the phase separator. In this example, the admission means of the sampling flask are connected to the phase separator in such a manner that said admission means are situated substantially in the middle of the level of the fluid phase for sampling inside said separator.

Firstly, the fact of using a separator in which the phases settle under gravity is a solution which is particularly simple and low in cost to implement; gravity separators are also robust, which means they can be used under conditions as severe as those which apply to testing effluents coming from oil wells. Secondly, the position of the admission means to the sampling flask guarantees that a pure fluid phase is recovered since this position is remote from the transition zones with the other phases of the multiphase fluid mixture within the separator after settling.

In a particularly advantageous implementation of the invention, the multiphase fluid mixture is a mixture comprising a majority hydrocarbon phase taken from a first separation step implementing a first phase separator on a multiphase effluent coming from an oil well, and the pipe is a pipe for recovering said mixture comprising said majority hydrocarbon phase under pressure conditions that corresponds to those which exist in said first phase sample.

The invention also provides sampling apparatus for taking a fluid phase from a multiphase fluid mixture flowing in a pipe under given pressure conditions, said apparatus comprising:
   a phase separator;
   admission means for admitting the multiphase fluid mixture into said separator; and sampling means for taking a sample of said fluid phase, said sampling means being connected to the phase separator.

According to the invention, said admission means also comprise closure means for increasing the pressure in the separator in successive stages.

Figure 2:
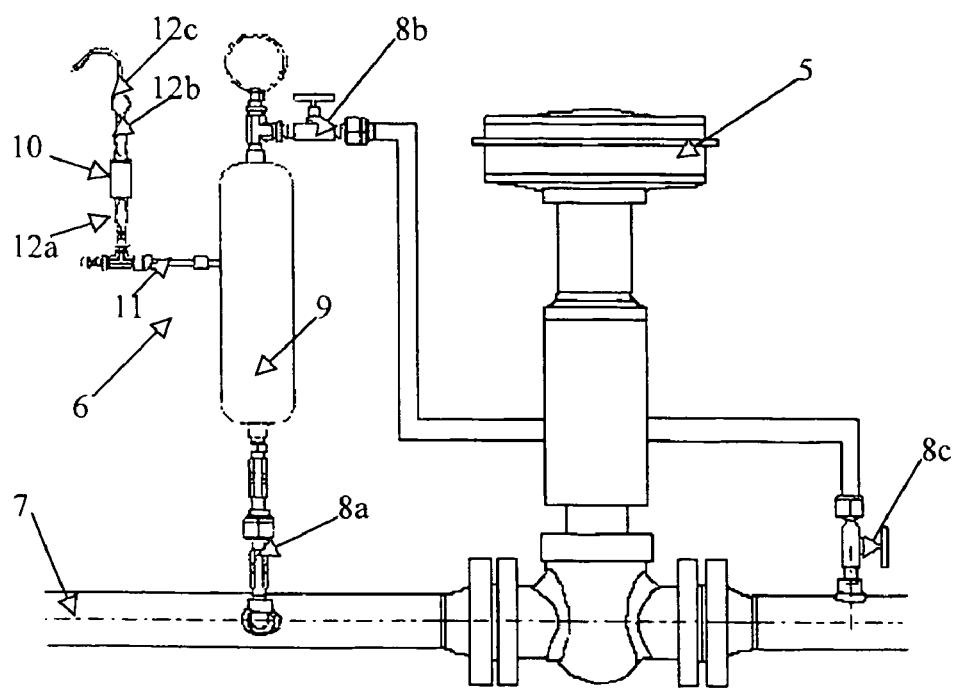

Other advantages and characteristics of the invention can be seen from the following description, given by way of example and with reference to the accompanying drawing, in which:

FIG. 1 is a diagrammatic view of an application of sampling apparatus of the invention; and FIG. 2 shows another application of sampling apparatus of the invention.

FIG. 1 shows an application of sampling apparatus of the invention. A main duct 1 receives an effluent from an oil well (not shown) to deliver it into a first gravity phase-separator 2. In the example shown, the separator 2 is a gravity phase-separator of the kind described in patent application No. 00/05666 filed on May 3, 2000 in the name of the Applicant. The separator provides first separation of the components of the effluent, i.e. its water, gas, and oil. As shown in FIG. 1, an oil recovery pipe 3 extends from substantially the middle of the oil phase inside the separator 2 to a "oil" circuit given overall reference 4. Depending on the type of first separator 2 that is used, the fluid mixture from the duct 3 flowing along the oil circuit can contain a greater or lesser percentage of water. In particular, when using a separator of the kind described in French patent application No. 00/05666, this mixture can contain gas, and its water content can be as much as 30%.

Head loss is implemented in the oil circuit 4 in the form of a level control valve 5 which serves to regulate the level of the multiphase fluid mixture in the first separator 2. The head loss caused by the control valve 5 also allows mixture from the first separator 2 to pass into a sampling device 6 of the invention, and shown in greater detail in the other application of FIG. 2. In FIG. 2, the fluid mixture circulates in any kind of pipe 7, possibly connected to a duct such as the duct 3 at the outlet from a separator 2. The sampling device is preferably connected in parallel with the pipe 7, but it could also be installed as a branch connection. Control valves 8a, 8b, and 8c govern the passage through the sampling device of the multiphase fluid mixture flowing along the pipe 7.

As shown in FIG. 2, the sampling device of the invention comprises a separator 9 which in this embodiment is a separator in which the phases settle under gravity. The sampling device 6 also comprises a sampling flask 10 which is connected via a connection valve 11 to the secondary separator 9 substantially halfway up said separator and more generally halfway up relative to the minimum height of the oil phase expected at the end of settling in the separator 9. This precaution makes it possible to be sure that the sample of the oil phase collected in the sampling flask is taken precisely from the desired phase, thereby guaranteeing a sample that is particularly pure. As a function of the way in which the phases are distributed in the multiphase fluid mixture, the position of the connection valve 11 along the separator 9 can be modified. The ends of the sampling flask 10 are provided with isolation valves 12a and 12b and with a gas evacuation valve 12c. Thus, by closing the valves 12a, 12b, and 12c, and by disconnecting the connection valve 11, it is possible to remove the sampling flask from the sampling apparatus of the invention in order to perform measurements. In particular, in order to discover the density of the oil phase, the set of valves 12a, 12b, and 12c (advantageously the valve 12c can be removable so as to further lighten the assembly) and the full sampling flask 10 is weighed. In order to ensure that the measurement is accurate, the weight of the sampling flask and of its isolation and evacuation valves is preferably as light as possible. Thereafter, in order to ensure that very pure oil is taken into the flask 10, it is advantageous to select a separator 9 that is much larger than said flask. Satisfactory results have been obtained with a separator whose capacity is 3 liters associated with a sampling flask whose capacity is 0.05 liters.

The sampling method of the invention is described below with reference to the above-described sampling apparatus. In general, the object of this method is to collect a sample of a pure fluid phase in a sampling flask 10 from a multiphase fluid mixture, e.g. effluent from an oil well. The collected sample should be under the same conditions of temperature and pressure as those which apply to the effluent flowing in the pipe 7. In the method, the ratio between the phases of the fluid mixture remains substantially stable over time, thus making it possible to dimension the sampling apparatus suitably, and in particular the size of the separator 9 and the position of the sampling flask 10.

In the application shown in FIG. 1, the effluent from the oil well is brought under given conditions of temperature T and pressure P into the first separator 2 where these conditions of temperature and pressure are not modified. A first separation step then follows in conventional manner after which the duct 3 is used to recover a first fluid mixture comprising a majority hydrocarbon phase still at the same conditions of pressure and temperature. After this first step, the fluid mixture whose phase ratio is substantially stable is directed to the oil circuit 4 by the pipe 7 at a rate which depends on the level control valve 5. The sampling method of the invention is then used to collect this mixture in the separator 9 while maintaining the same conditions of temperature T and pressure P in the pipe 7. Should these conditions vary, particularly should the pressure in the secondary separator 9 be lower than the pressure in the pipe 7, then the primary mixture would depressurize and the resulting oil phase would be "dead" oil that is not suitable for determining the production capacity of the oil well.

The sampling flask is initially connected to the secondary separator via the connection valves 11. The sampling flask is previously brought to the temperature and pressure T and P, and its isolation valves 12a, 12b, and 12c closed. To pressurize the sampling flask, it can very simply be connected via the valve 12a to the gas outlet from the primary separator, with the gas being allowed to flow by opening the valves 12b and 12c a little and then closing these two valves. The flask is filled with gas under the conditions T and P. It is also possible to use external compressor means. Once the sampling flask 10 has been connected, the valves 8a, 8b, and 8c are opened to allow the primary fluid mixture from the pipe 7 to flow through the separator 9. Thereafter action is taken on the control valve 8b to close it progressively so as to raise the pressure in the separator 9 in stages. In this way, the first quantity of fluid mixture will depressurize because the valves 8a, 8b, and 8c are fully open and the volume inside the separator is empty. Thereafter, this first quantity flows through the separator and by closing the valve 8b a little, a new quantity of mixture as admitted thereto will depressurize less because the pressure inside the separator 9 has increased. In addition, this new quantity of mixture will serve to evacuate a fraction of the initial dead oil that has formed. By proceeding in this way, closing valves in successive stages, and thus increasing pressure successively, the separator is eventually filled with a multiphase fluid mixture which loses less and less pressure and which progressively expels smaller and smaller quantities of dead oil. Once the control valve 8b has been completely closed, the secondary separator is full of fluid mixture, comprising a majority hydrocarbon phase, and under the appropriate conditions of temperature and pressure, T and P.

The fluid mixture is then allowed to settle in the secondary separator. After a certain length of time has elapsed, this mixture will have split into three phases: a gas phase at the top of the separator, an oil phase in the middle, and a water phase in the bottom of the separator. The oil phase is then particularly pure and suitable for measuring density and/or shrinkage since the time required for settling has not been influenced by the flow of mixture in the pipe 7, so settling time can be relatively long. After this rest time, the connection valve 11 is opened slowly together with the isolation valve 12a so as to connect the sampling flask 10 to the oil phase in the separator 9. The oil phase is still at the given conditions T and P. The isolation valve 12b is then opened and the gas evacuation valve 12c is opened very slightly (by way of example, this valve can be a precision, needle valve) so that the oil phase penetrating into the sampling flask can expel the gas. In this way, the flask is filled with oil that is very pure and that is at the same pressure conditions as the pipe 7 (which are likewise the same as those in the first separator 2, in the application shown in FIG. 1).

As soon as the first drop of oil appears at the outlet from the sampling flask, the valves 12b and 12c are closed. It is then possible to close the valve 12a and the valve 11, and to open a purge valve (not shown) between these two valves, thus making it possible to recover the sampling flask filled with oil phase at appropriate pressure and temperature conditions. It is then possible, for example, to measure the density of the oil under the conditions that exist in the pipe 7. To do this, it suffices to weigh the full flask (after cleaning its ends to remove any oil that has not come from inside the flask). Since the flask was previously weighed when empty, the density $\rho_o^{P,T}$ of the oil in grams per cubic centimeter (g/cm$^3$) under the conditions P and T is thus given by:

$$\rho_o^{P,T} = \frac{M_o}{V_{fla}}$$

where $M_o$ in grams is the mass of the oil and $V_{fla}$ in cm$^3$ is the (calibrated) volume of the flask.

The oil can then be depressurized by opening the valve 12b, with the gas contained in this oil phase escaping so as to obtain "dead" oil under atmospheric conditions of temperature and pressure. By taking the ratio of the volumes of oil at P and T and at $P_{atm}$ ad $T_{atm}$, it is possible to calculate the shrinkage Srkg of the oil as follows:

$$Srkg = \frac{V_o^{P_{atm},T_{atm}}}{V_o^{P,T}}$$

where $V_o^{P_{atm}T_{atm}}$ is the volume of oil collected under atmospheric conditions and $V_o^{P,T}=V_{fla}$ is the volume of oil under the conditions in the pipe 7. The shrinkage and the density of the oil under the temperature and pressure conditions in the pipe 7 then make it possible to determine the volume flow rate of the oil under atmospheric conditions on the basis of its mass flow rate (as measured by instruments, not shown, installed in the pipe 7).

It is also possible to calculate this shrinkage accurately using measurements of oil mass after depressurization, M'$_o$, and of oil density under atmospheric conditions (using a density meter), $\rho_o^{P_{atm},T_{atm}}$. The shrinkage is then given by the following relationship:

$$Srkg = \frac{V_{atm}}{V_{fla}} = \frac{M_o}{\rho_o^{P_{atm},T_{atm}} \times V_{fla}}$$

where $V_{fla}$ is the volume of oil collected in the sampling flask.

The sampling method and the associated apparatus of the invention thus make it very simple and reliable to correct a measurement performed under certain thermodynamic conditions P and T on effluent from an oil well so as to obtain a usable result concerning the production perspectives of said well under "standard" thermodynamic conditions close to atmospheric conditions. This method is particularly effective when there is a first separator 2 upstream from the pipe 7 with the outlet from the first separator providing a fluid mixture that contains a percentage of water that is not negligible but that is substantially stable. In addition, the method and the apparatus of the invention make it possible to sample any effluent-exporting pipe under thermodynamic conditions which is an essential factor in ensuring that calculations performed on the recovered sample are pertinent.

The invention claimed is:

1. A method of sampling a fluid phase in a multiphase fluid mixture flowing in a pipe under given pressure conditions, said method comprising the following steps:
   admitting the multiphase fluid mixture into a phase separator;
   separating the multiphase fluid mixture so as to isolate the fluid phase for sampling;
   pressurizing a sampling device to the given pressure in the pipe;
   recovering a sample of said fluid phase in said sampling device; and
   increasing the pressure in the phase separator in successive stages until said pressure in the separator reaches the give pressure in the pipe.

2. A method according to claim 1, wherein the step of increasing of pressure by successive stages is performed simultaneously with the step of admitting the multiphase fluid mixture into the separator.

3. A method according to claim 1, wherein the phase separator comprises a separator in which the phases settle under gravity.

4. A sampling method according to claim 1, wherein the sampling device comprises a sampling flask and admission valves, said admission valves being connected to the phase separator.

5. A sampling method according to claim 1, wherein the distribution of phases in the multiphase fluid mixture flowing in the pipe at the given pressure is substantially stable over time.

6. A sampling method according to claim 1, wherein the sampling device comprises a sampling flask and admission valves, said admission valves being connected to the phase separator, wherein the distribution of phases in the multiphase fluid mixture flowing in the pipe at the given pressure is substantially stable over time and wherein the admission valves of the sampling flask are connected to the phase separator in such a manner that said admission valves lie substantially in the middle of the level of the fluid phase for sampling inside said separator.

7. A method according to claim 1, wherein the multiphase fluid mixture is a mixture comprising a majority hydrocarbon phase taken from a first separation step implementing a first phase separator on a multiphase effluent coming from an oil well, and the pipe is a pipe for recovering said mixture comprising said majority hydrocarbon phase under pressure conditions that corresponds to those which exist in said first phase sample.

8. Sampling apparatus for taking a fluid phase from a multiphase fluid mixture flowing in a pipe under given pressure conditions, said apparatus comprising:
   a phase separator;
   admission valves for admitting the multiphase fluid mixture into said separator;
   removable sampling device for taking a sample of said fluid phase in said phase separator; and
   closure valves for increasing the pressure inside the separator in successive stages and wherein the distribution of phases in the multiphase fluid mixture is substantially stable over time and wherein the sampling device comprises a sampling flask connected to the separator via admission valves such that said valves are situated substantially in the middle of the level of the fluid phase for sampling inside said separator.

9. Sampling apparatus according to claim 8, wherein the phase separator comprises a separator in which the phases settle under gravity.

10. Apparatus according to claim 9, wherein the multiphase fluid mixture is a mixture comprising a majority hydrocarbon phase coming from a first separation step implemented by means of a first phase separator acting on a multiphase effluent coming from an oil well, and the pipe is a pipe for recovering said mixture comprising said majority hydrocarbon phase under conditions of pressure that correspond to those that exist inside said first phase separator.

11. Apparatus according to claim 8 wherein the multiphase fluid mixture is a mixture comprising a majority hydrocarbon phase coming from a first separation step implemented by means of a first phase separator acting on a multiphase effluent coming from an oil well, and the pipe is a pipe for recovering said mixture comprising said majority hydrocarbon phase under conditions of pressure that correspond to those that exist inside said first phase separator.

12. A method according to claim 2, wherein the phase separator comprises a separator in which the phases settle under gravity.

13. A sampling method according to claim 3, wherein the sampling device comprises a sampling flask and admission valves, said admission valves being connected to the phase separator.

14. A sampling method according to claim 13, wherein the distribution of phases in the multiphase fluid mixture flowing in the pipe at the given pressure is substantially stable over time.

* * * * *